United States Patent [19]

Cicchiello et al.

[11] Patent Number: 5,044,754

[45] Date of Patent: Sep. 3, 1991

[54] APPARATUS AND METHOD FOR USE IN DETERMINING THE OPTICAL TRANSMISSION FACTOR OR DENSITY OF A TRANSLUCENT ELEMENT

[75] Inventors: James M. Cicchiello; Tomi Lahcanski, both of Rochester, N.Y.

[73] Assignee: Eastman Kodak Company, Rochester, N.Y.

[21] Appl. No.: 453,530

[22] Filed: Dec. 20, 1989

[51] Int. Cl.$^5$ .......................... G01N 21/59; G01J 1/04
[52] U.S. Cl. ..................................... 356/432; 356/236; 356/443
[58] Field of Search ............... 356/432, 435, 436, 443, 356/444, 236, 234; 250/228

[56] References Cited

U.S. PATENT DOCUMENTS

| | | | |
|---|---|---|---|
| 3,827,808 | 8/1974 | Cho | 356/199 |
| 4,012,144 | 3/1977 | Hedelman | 356/73 |
| 4,575,252 | 3/1986 | Akiyama | 356/446 |
| 4,687,336 | 8/1987 | Pumphrey et al. | 356/436 |

Primary Examiner—Vincent P. McGraw
Assistant Examiner—LaCharles P. Keesee
Attorney, Agent, or Firm—Francis H. Boos, Jr.

[57] ABSTRACT

Apparatus and method are described for determining the transmission factor or the density of a translucent element, such as an optical filter, using the cosine-to-the-fourth law. The apparatus includes a source of light of constant color and intensity. A detector is mounted on a track for movement along rectilinear path with the plane of the operative face of the detector parallel to the path. A reading of the intensity of light from the source sensed by the detector is taken in one position with the element in the light path and in another position with the element absent. The positions being such that the two readings are equal. The angles $\Theta$ and $\alpha$ of incidence of light on the detector in the two positions are determined and computer means determine value of $$\frac{\cos^4 \Theta}{\cos^4 \alpha}$$

to give the value of the transmission factor.

28 Claims, 4 Drawing Sheets

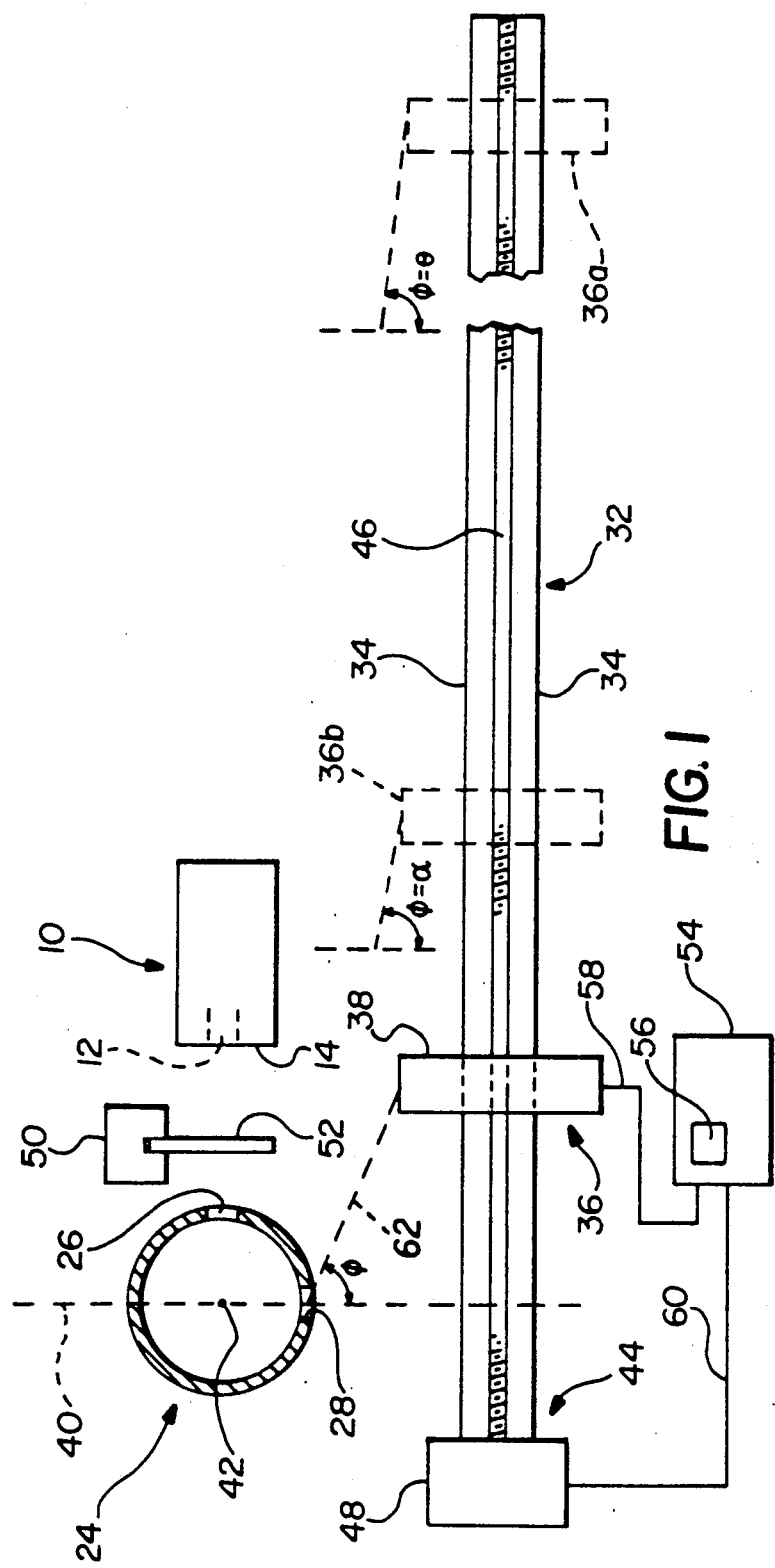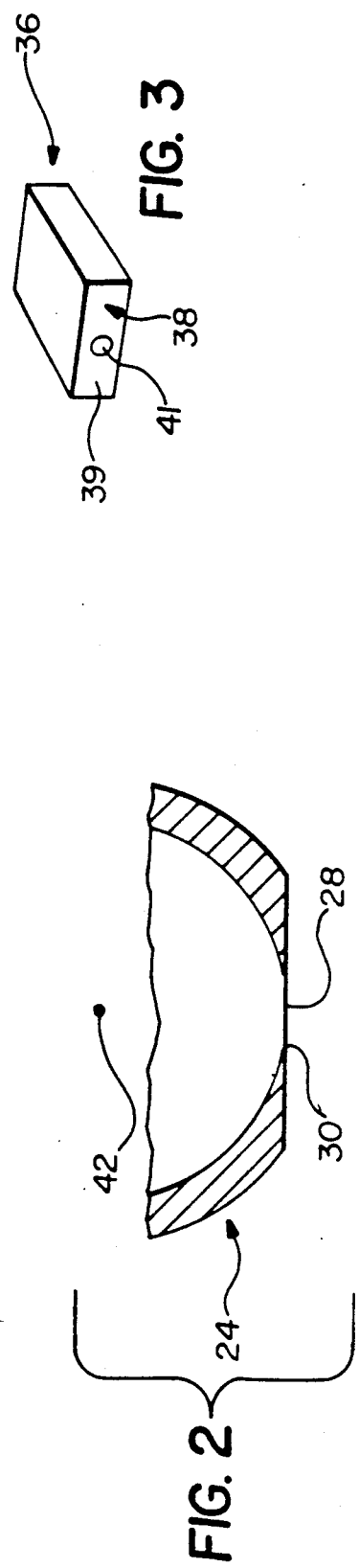

APPARATUS AND METHOD FOR USE IN DETERMINING THE OPTICAL TRANSMISSION FACTOR OR DENSITY OF A TRANSLUCENT ELEMENT

BACKGROUND OF THE INVENTION

1. Field of the Invention

This invention relates to apparatus and methods for use in determining the optical transmission factor or density of translucent elements, such as, for example, optical filters.

2. The Prior Art

It is known to determine the optical transmission factor, or density, of translucent elements, such as filters for use in testing photographic materials during manufacture, by using the inverse square law bench. As is well known, the inverse square law states that the intensity of illumination due to a point source is proportional to the square of the distance from the source. With the inverse square law bench, the intensity of a source is measured at distance $R_1$ with a detector. The translucent element whose transmission factor is to be determined is then inserted between the source and the detector. The detector is then moved towards the source until it senses an intensity equal to that which it sensed at distance $R_1$ without the element in the path. The distance at this new location of the detector is $R_2$. The transmission factor of the element is given by:

$$R_2^2/R_1^2$$

If the inverse square law bench is to be of reasonable size it has a very limited dynamic range. In order to extend the dynamic range, it is known to insert a standard filter, or filters, in the path between the source and the detector during the portion of the determination in which the test element is not in the path. This procedure is sometimes termed "bootstrapping". The use of standard filters in this way has been found to introduce errors and has made the test procedure costly on labor.

It is an object of the present invention to reduce the problems of the prior art by providing method and apparatus for determining the transmission factor or density of translucent optical elements which are both more accurate and less labor intensive.

SUMMARY OF THE INVENTION

The object of the invention is achieved by providing apparatus and methods which rely on the cosine-to-the-fourth law rather than the inverse square law.

Thus, apparatus in accordance with the present invention comprises a source of light of constant color temperature and constant intensity and means for mounting an element to be tested in the path of light from the source. There are detector means having an operative face and adapted to provide a signal indicative of the intensity of light incident on the operative face. Also, there are track means for mounting the detector means for movement along a rectilinear path with the plane of the operative face of the detector means being parallel to the rectilinear path. The track means is so disposed relative to the source of light that in one position of the detector means on the track means, light from the source is incident normally on the operative face of the detector means. Further, there are means for determining the position of the detector along the track means.

Apparatus in accordance with one embodiment of the present invention comprises an integrating sphere having an inlet and an outlet defined by a knife edge. There are means for introducing light of constant color and intensity into the integrating sphere through the inlet. Means are provided for mounting the element to be tested in the path of light to the inlet of the sphere. A detector is provided having an operative face and adapted to provide a signal indicative of the intensity of light incident on it. There are knife-edged mask means bounding an aperture on the operative face of the detector. The apparatus further includes track means for mounting the detector for movement along a rectilinear path perpendicular to a radial line passing through the center of the sphere and the center of the outlet. It is arranged that the operative face of the detector faces the outlet of the integrating sphere when the radial line passes through the aperture on the operative face of the detector. There are means for moving the detector along the track and means for determining the position of the detector along the track.

In one embodiment, the means for determining the position of the detector along the track means is adapted to provide a signal indicative of angle $\Phi$ between the radial line and a line intersecting the radial line, the outlet and the aperture.

In an advantageous embodiment of the invention, there are means for positioning the detector at a datum position whereat the angle $\Phi$ has a value $\Theta$. There are means for recording the intensity of light sensed by the detector at the datum position without the element in the light path. Also, there are means for controlling movement of the detector to a position of equality whereat the intensity of light detected by the detector with the element in the light path is the same as the intensity recorded with the detector at the datum position and without the element in the light path.

Advantageously, the apparatus includes means for performing the calculation of the value of $$\frac{\cos^4\Theta}{\cos^4\alpha}$$

wherein:
  $\Theta$ is the value of $\Phi$ when the detector is at the datum position; and
  $\alpha$ is the value of $\Phi$ when the detector is at the position of equality.

The present invention also resides in a method for determining the optical transmission factor of a translucent element which includes the steps of providing an integrating sphere having an inlet and a knife-edged outlet and providing a source of light of constant intensity and color. Light is directed from the source into the sphere through the inlet. The method also includes providing a detector having an operative face and a knife-edged aperture on the operative face, the detector being adapted to provide a signal indicative of the intensity of light incident on its operative face. Means are provided for moving the detector along a rectilinear path perpendicular to a radial line passing through the center of the sphere and the outlet and so disposed that in one position of the detector the operative face is intersected by, and is perpendicular to, the radial line. The method also includes the step of positioning the detector in a datum position on the path so that the angle $\Phi$ between a line intersecting the outlet, the radial line and the operative face and the radial has a value $\Theta$. The method includes gaining from the detector a signal indicative of the intensity of light incident on it from the sphere when the detector is at the datum position. The element to be tested is then inserted in the path of light from the source to the sphere. Then, the detector is moved along the track until the signal generated by the detector, with the element in the light path, is the same as that generated by the detector when at the datum position. The detector is then in a position of equality in which the angle $\Phi$ has a value $a$. Computer means are then used to calculate the value of $$\frac{\cos^4\Theta}{\cos^4 a}$$

to determine the transmission factor of the element.

In one embodiment of the method of the present invention, which is intended for determining the optical transmission factor of a translucent element at a particular wavelength or band of wavelengths, there is the additional step of inserting a standard filter into the path of light from the source to the sphere prior to the taking of any measurements. The standard filter is adapted to pass substantially only the particular wavelength or band of wavelengths.

In another embodiment of the method of the present invention, the element to be tested is placed in the path of light from the integrating sphere to the detector. In this case, the reading of the intensity of light received by the detector with the element to be tested in the light path, is made with the light incident normally on the detector, i.e. with an incidence angle of 0 degrees. This zero angle of incidence avoids problems due to variability of reflections off the element, variability of effective thickness of the element, and internal reflection, which would occur with the incidence angle being other than zero and variable.

In an embodiment of the present invention for determining the optical density of the translucent element, there is the additional step of determining with computer means the value of the log of the reciprocal of the value of the transmission factor.

Embodiments of the present invention will now be described, by way of example, with reference to the accompanying drawings, in which:

BRIEF DESCRIPTION OF THE DRAWINGS

FIG. 1 is a schematic plan view of apparatus in accordance with the present invention, with the integrating sphere being shown in section;

FIG. 2 is a sectional view of a portion of the integrating sphere, illustrated in FIG. 1, showing the knife edge bounding the outlet;

FIG. 3 is a perspective view of the detector, included in the apparatus represented in FIG. 1, and showing a knife-edged aperture on the operative face thereof;

FIG. 7, comprising

DESCRIPTION OF A PREFERRED EMBODIMENT

Figure 5:
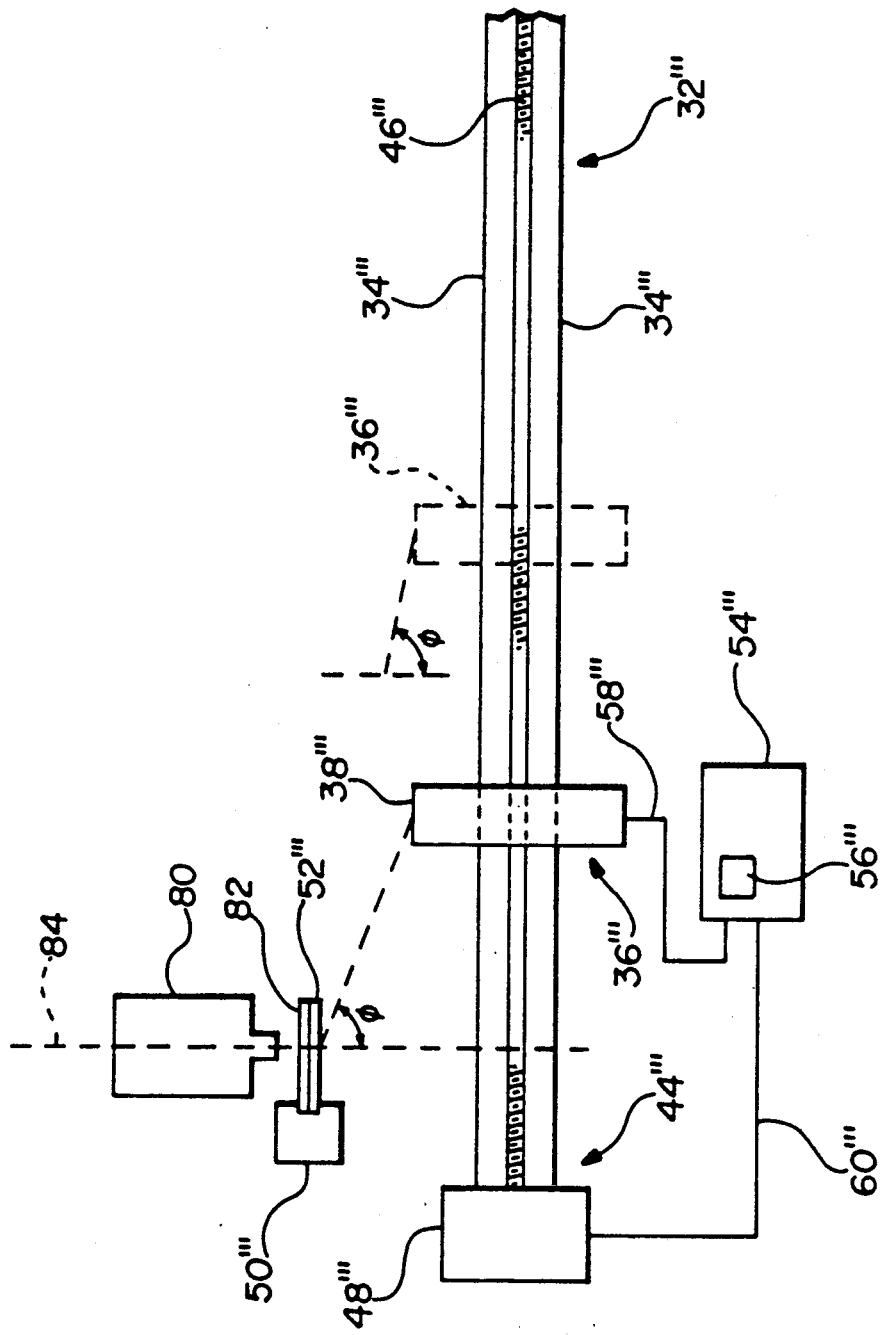
FIG. 5 is a schematic plan view, similar to FIG. 1, of a third embodiment of the present invention.

Apparatus in accordance with the present invention and for performing methods in accordance with the present invention, is illustrated in the accompanying drawings. Reference is now made to FIG. 1. In which there is illustrated a light source housing 10 containing a light source of constant color temperature and intensity. An example of such a light source is described in copending U.S. patent application Ser. No. 279,628 filed Dec. 5, 1988. The housing 10 has an outlet, indicated at 12, in its left end wall 14.

The apparatus further includes an integrating sphere 24 which has an inlet 26 facing the outlet 12 of the light source housing 10, and an outlet 28. The outlet 28 is a circular aperture which, as may be seen in the enlarged view of FIG. 2, is bounded by a knife edge 30. The aperture may be other than circular but it is desirable that its shape be easily described mathematically. The light source housing 10 and integrating sphere 24 combined form a lambertian source of light, a feature which is important to the functioning of the cosine-to-the-fourth law in the present invention. As is known, the output of a lambertian light source is of constant radiance defined in optics as the radiant light flux per unit solid angle per unit of projected area of the source.

Also included in the apparatus are track means 32 which include a pair of parallel rectilinear rails 34. Mounted on the rails for movement along them, is a detector 36. The detector has an operative face 38 for receiving light, which is disposed in a plane parallel to the rectilinear lines of the rails 34. The operative face 38 of the detector 36 has printed on it an opaque mask 39. The mask 39 bounds an aperture 41 (see FIG. 3). In that the mask 39 is printed on the operative face 38, the aperture 41 has a knife edge by virtue of the thinness of the print.

The rectilinear lines of the rails 34 lie in planes perpendicular to a line 40 which passes through the center 42 of the integrating sphere 24 and the center of the outlet 28. The line 40 is perpendicular to the plane of the operative face 38 of the detector 36.

The detector is moved along the track by moving means 44 which includes a screw-threaded shaft 46 which is disposed parallel to the rails 34 and is engaged by a nut (not shown) associated with the detector 36. The shaft 46 is driven in rotation by a stepper motor 48 which includes feedback means (not shown) for determining the position of the detector 36.

Support means 50 are provided for supporting a translucent element 52 to be tested, in the path of light from the light source housing 10 to the inlet 26 of the integrating sphere 24.

A computer 54 with a readout 56 receives signals from the detector 36 through a lead 58 and from the stepper motor 48 through lead 60. The amplifier for the detector 36 is mounted on the travelling detector and only a digital signal is fed along lead 58. The detector 36 may be a seven decade silicon photodiode, for example, one manufactured by Hamamatsu under the model number 1227. The amplifier may be one manufactured by Burr-Brown under the model number OPA 128LM.

The angle between the radial line 40 and a line 62 which intersects the radial line 40, the center of the outlet 28 from the integrating sphere 24 and the center of the aperture 41 in the mask 39 on the operative face 38 of the detector 36, is, generically, termed Φ.

The track means 32 is positioned at such a distance form the integrating sphere 24 and is of such a length that when the detector is at the remote end of the track means 32 (termed the "datum position" and shown in broken lines at 36a in FIG. 1) the limiting value of Φ, termed Θ, approaches 89°. In one embodiment, the effective length of the track means 32 is three meters and the path of the operative face of the detector is about 10 cms from the knife-edged outlet 28 of the integrating sphere 24 when the detector 36 is so disposed on the track means 32 that the line 40 passes through the aperture 41 in the mask 39 on the operative face of the detector.

All of the apparatus except, perhaps, for the computer, is mounted on an optical vibration isolation bench, to isolate the apparatus from vibrations.

In performing a method in accordance with the present invention, using the above-described apparatus, the light source in the light source housing 10 is energized and stabilized. The detector 36 is moved to its datum position, shown in broken lines at 36a in FIG. 1. At this time, the element 52 to be tested is not in its support means. The computer records the value of the intensity of light from the integrating sphere, detected by the detector. The computer also records the position of the detector along the track means.

The translucent element 52 is now inserted in its support means 50 and the detector is moved by the stepper motor 48 back along the track means 32 until the signal from the detector is the same as that when the detector was at its datum position (shown in broken lines at 36b in FIG. 1 and termed the position of equality). The value of angle Φ is now α. The position of the detector 36b in the position of equality is determined from signals received from the stepper motor 48.

The computer converts the information about the lineal position of the detector at the datum position 36a and the position 36b of equality into the angular values Θ and α and performs the computation of the function $$\frac{\cos^4 \Theta}{\cos^4 \alpha}$$

which gives the value of the transmission factor of the filter.

If the density of the filter is required, the computer is programmed to perform the additional computation of $$\mathrm{Log}\left[\frac{1}{\text{transmission factor}}\right]$$

If a step wedge filter, such as is used in the testing of photographic film and paper, is to be tested, the method described above is repeated for each of the steps.

If the transmission factor or density of a translucent element at a particular wavelength or band of wavelengths is to be measured, then a standard filter passing that wavelength or band of wavelengths is inserted in the support means 50 both for the intensity reading at the datum position and for the reading when the position of equality 36″ is found, the test element being added in the support means for the finding of the position of equality, of course. At least for such tests, it is to be understood that the statement herein that the light source is of constant color temperature is to be understood as meaning that the light source has constancy in at least the frequencies which are pertinent in the test.

Some standards state that the test element must be backed by a lambertian transmitting element, sometimes referred to as an opal glass. If it is desired to use an opal glass, the support means 50 is adapted to mount both the test element and the opal glass.

Figure 4:
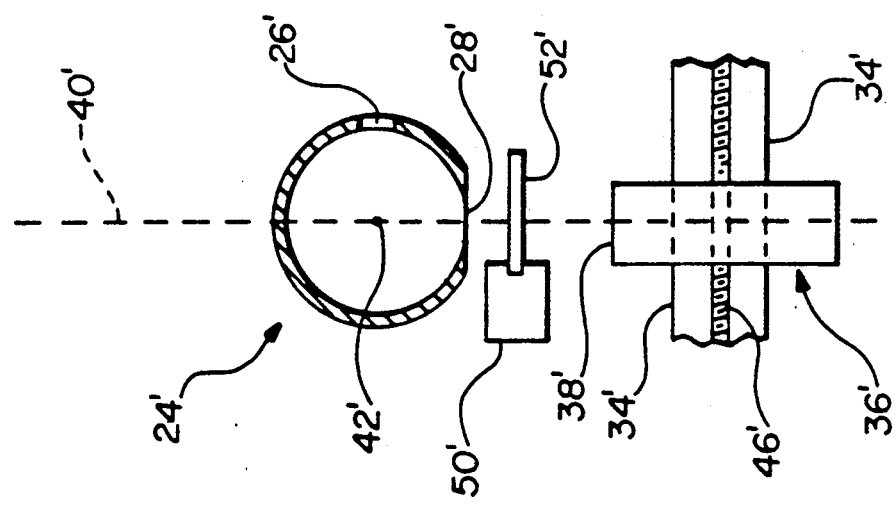
FIG. 4 is a schematic plan view of a portion of an apparatus in accordance with a second embodiment of the present invention, and is similar to a portion of FIG. 1.

In the embodiment described above, the element to be tested is disposed between the light source 10 and the inlet 26 to the integrating sphere 24. FIG. 4 illustrates a portion of an embodiment, otherwise similar to that illustrated in, and described with reference to, FIG. 1, but differing in that in the embodiment illustrated in FIG. 4 the element to be tested is disposed adjacent the outlet 28′ of the integrating sphere 24′. Parts illustrated in FIG. 4 are given the same reference numeral as the parts to which they correspond in FIG. 1 but with the addition of a prime (′) suffix. For a complete understanding of the remainder of the embodiment illustrated in FIG. 4, reference is directed to the description above with reference to FIG. 1. If the method of testing described above with reference to FIG. 1 were to be adopted in this embodiment, the light passing through the element towards the detector would be inclined to the plane of the element. This would introduce several problems, such as reflection at the surface varying with angle, internal reflection variations, and thickness of the element varying with angle. To avoid these problems, the reading with the element in the light path is taken when the light is incident normally on the operative surface 41 of the detector, that is, with the radial line 40′ through the center of the sphere and the center of the outlet aperture 28′ being perpendicular to the plane of the operative face of the detector. In this condition, the value of Φ is zero. After the value of the intensity of the light incident on the detector with Φ=0°, the filter element is removed and the detector is moved along the track 32′ until the value of the intensity of light incident on the operative face of the detector is equal to that recorded at Φ=zero with the element in the light path. The value, α, of Φ at this position of equality is determined and the computer computes the value of $$1/\cos^4 \alpha$$

to give the transmission factor. Of course, in this embodiment also, an opal glass could be positioned against the test element, as required by certain standards.

In another embodiment of the present invention schematically represented in FIG. 5, the parts are given the same reference numerals as corresponding parts in the embodiments described above but with the addition of a triple prime(‴) suffix. Only those aspects of this embodiment which differ from the previously described embodiments will now be described. Reference should be made to the foregoing description for an understanding of aspects not now to be described. In the embodiment illustrated in FIG. 5, there is a light source 80 which directs light at an element 52‴ which is carried by mounting means 50‴ and is backed by an opal glass 82. The opal glass 82 serves in this embodiment to convert the light source 80 into a lambertian source of light required for proper application of the cosine-to-the-fourth law in the present invention. Line 84 is perpendicular to the lines of the tracks 34‴ and to the plane of the operative face 38''' of the detector 36'''. In this embodiment, as in the embodiment partially illustrated in FIG. 4, the value of the intensity of light incident on the detector 36''' with the element 52''' in the light path is taken with $\Phi=0°$. That value is recorded by the computer means 54'''. The element 52''' is then removed and the detector is moved along the track by the stepper motor 48''' until the value of the intensity of the light incident on the operative face of the detector is equal to the recorded value. The detector is then in the position of equality. The value of angle $\Phi$ is determined and the computer means computes the value of the transmission factor by computing $$1/\cos^4\alpha$$

Figure 6:
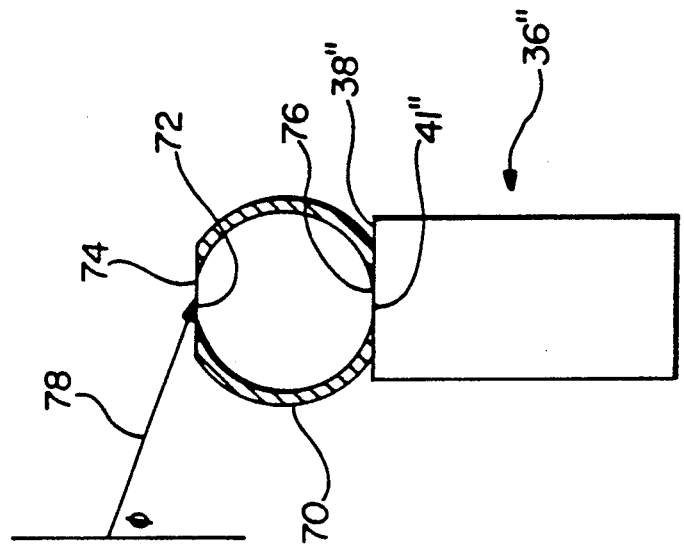
FIG. 6 is a schematic representation of a detector and integrating sphere, shown in section, usable in embodiments of the present invention.

The above description of the computation does not take into account the effect of the varying angle of incidence of the light on the detector 36. The varying angle of incidence leads to a variation in the ratio of the portion of incident light which is absorbed into the detector and the portion which is reflected. This leads to a small but meaningful error. This error can be removed by using an appropriate anti-reflection coating on the face of the detector or by including in the computer additional software which factors in the angle of incidence on the detector or by including an integrating sphere in the detecting means, as illustrated in FIG. 6. FIG. 6 shows detector means 70 including a detector 36" having an operative face 38" with an aperture 41". An integrating sphere 70 is mounted on the operative face 38" and has an inlet aperture 72, bounded by a knife edge 74, and an outlet aperature 76 in register with the aperture 41" of the detector 36". A light ray 78 is shown entering the integrating sphere 78.

Figure 7C:
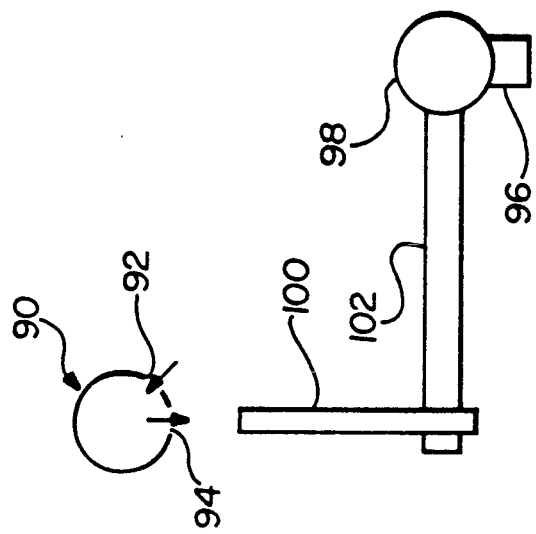
FIGS. 7a, 7b and 7c, shows, schematically, a fourth embodiment of the present invention.
Figure 7B:
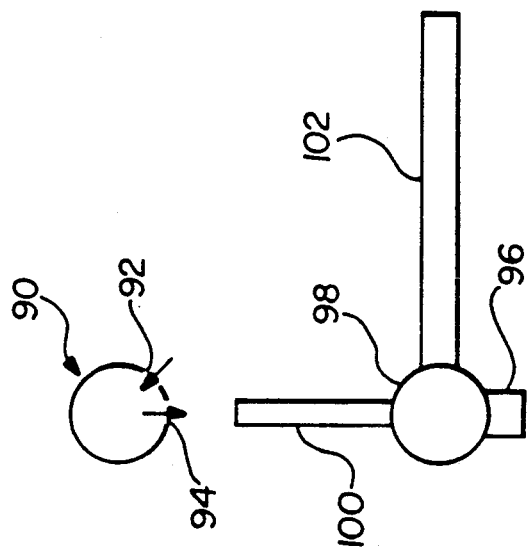
Figure 7A:
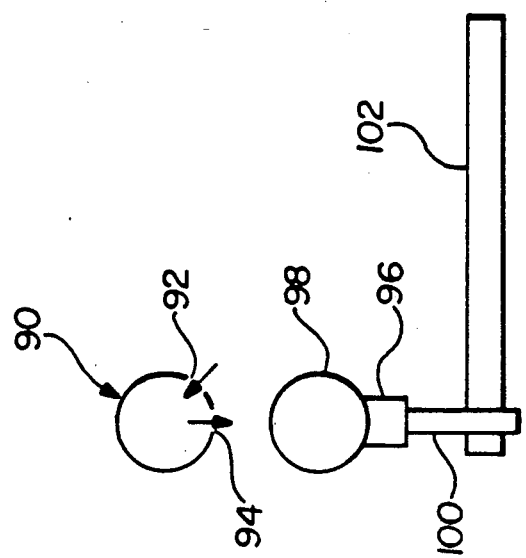

Yet another embodiment of the present invention is intended to allow both adoption of square law testing and cosine-to-the-fourth law testing. FIG. 7 schematically represents such an embodiment. For parts not illustrated in or described with reference to FIG. 7, reference should be had to the foregoing descriptions of other embodiments. In FIG. 7 there is illustrated an integrating sphere 90 similar to the sphere 24, which receives constant intensity and constant color temperature light from a source, not shown, through inlet aperture 92. The sphere 90 has an outlet aperture 94. A detector 96, similar to detector 36, has an integrating sphere 98 associated with its operative face similarly to the arrangement illustrated in and described with reference to FIG. 6. Two track means are provided. A first track means 100 extends parallel to a line, such as line 40, which passes through the center of the sphere 90 and of the outlet aperture 94. The second track means 102 is similar to the track means of the previously described embodiments and is perpendicular to the first track mean 100. In FIG. 7a the detector 96 and its integrating sphere 98 are disposed as close as possible to the sphere 90 and it is in this position that the reading with the element to be tested in the light path is taken. The element to be tested is then removed and the detector and its sphere are backed off along the first track means until a position of equality is found. Assuming the position of equality is found, the value of the transmission factor is determined by the inverse square law. If a position of equality is not found with the detector on the first track means, the detector and its sphere transfer to the second track means and are moved along that until the position of equality is found.

Assuming:
$R_1$ is the distance of the detector from the element when the first reading is taken;
$R_2$ is the maximum distance of the detector from the element on the first track means and is the distance of the detector from the element as it starts its movement along the second track means;
$\alpha$ is the angle of the light incident on the detector sphere to the line of the first track means, when the detector is in the position of equality;
the transmission factor is given by $$\frac{R_1^2}{R_2^2} \cdot \frac{1}{\cos^4\alpha}$$

In the description above, it is said that the track means includes two rails. It will be understood by those skilled in the art that other forms of track means, for example a single rail, may be employed. Also, the moving means have been described as being a stepper motor and a screw-threaded shaft. Those skilled in the art will recognize that other forms of moving means may be adopted, for example a linear stepper motor. Also, the detector may be moved and its position determined by an optical encoder.

The invention has been described in detail with particular reference to preferred embodiments thereof, but it will be understood that variations and modifications can be effected within the spirit and scope of the invention.

What is claimed is:

1. Apparatus for use in determining the optical transmission factor or density of a translucent element using the cosine-to-the-fourth law, including:
   a source of lambertian light of constant color temperature and constant radiance;
   means for mounting the element to be tested in position to affect the light from said source;
   detector means having an operative face and adapted to provide a signal indicative of the intensity of light incident on the operative face;
   track means for mounting the detector means for movement along a rectilinear path, the plane of the operative face of the detector means being parallel to the rectilinear path, the track means being so disposed relative to the source of light that in one position of the detector means on the track means, light from the source is incident normally on the operative face of the detector means and, at other positions on the track means said light is incident at an angle to the detector operative face; and
   means for determining the position of the detector means along the track means.

2. Apparatus as claimed in claim 1, including:
   an integrating sphere having an inlet aperture for light from the source and an outlet aperture, said means for mounting the element for testing being disposed between the source and the inlet aperture of the sphere.

3. Apparatus as claimed in claim 2, wherein light source includes a non-lambertian light source and means for mounting a lambertian transmitting element between the means for mounting the element and the non-lambertian light source.

4. Apparatus as claimed in claim 2, wherein the outlet aperture of the sphere is circular and has a knife edge.

5. Apparatus as claimed in claim 1, including:

an integrating sphere having an inlet aperture for light from the source and an outlet aperture, said means for mounting the element being disposed adjacent the outlet aperture of the sphere.

6. Apparatus as claimed in claim 1, wherein the means for mounting the element to be tested is adapted to mount the element in a plane parallel to the plane of the operative face of the detector means.

7. Apparatus as claimed in claim 6, wherein the light source includes means for mounting a lambertian transmitting element adjacent an element mounted in the means for mounting the element to be tested.

8. Apparatus as claimed in any one of the preceding claims, wherein the means for determining the position of the detector means along the track means is adapted to provide a signal indicative of angle $\Phi$ between the direction of the light when incident normally on the operative face of the detector means and the direction of the light incident on the operative face of the detector means at the position.

9. Apparatus as claimed in any one of claims 1-5, 6 and 7, including an anti-reflection coating on the operative face of the detector means.

10. Apparatus as claimed in any one of claims 1-5, 6 and 7, wherein the detector means includes an integrating sphere and a detector, said integrating sphere of the detector means having an inlet aperture of circular form and with a knife edge and an outlet aperture providing a path for light from the sphere to the detector, the inlet aperture of the integrating sphere of the detector means constituting said operative face of the detector means.

11. Apparatus as claimed in claim 2, wherein the means for determining the position of the detector means along the track means is adapted to provide a signal indicative of angle $\Phi$ between the direction of the light when incident normally on the operative face of the detector means and the direction of the light incident on the operative face of the detector means at the position, including means for positioning the detector means at a datum position whereat the angle $\Phi$ has a value theta, means for recording the intensity of the light sensed by the detector means at the datum position without the element in the light path, and means for controlling movement of the detector means to a position of equality whereat the intensity of light detected by the detector means with the element in the light path is the same as the intensity recorded with the detector at the datum position and without the element in the light path.

12. Apparatus as claimed in claim 11, including means for performing the calculation of the value of $$\frac{\cos^4\theta}{\cos^4\alpha}$$

wherein:
theta is the value of $\Phi$ when the detector means is at the datum position; and
$\alpha$ is the value of $\Phi$ when the detector means is at the position of equality.

13. Apparatus as claimed in claim 2, wherein the means for determining the position of the detector means along the track means is adapted to provide a signal indicative of angle $\Phi$ between the direction of the light when incident normally on the operative face of the detector means and the direction of the light incident on the operative face of the detector means at the position, including means for positioning the detector means at a datum position whereat the light is incident normally on the operative face of the detector means and the angle $\Phi$ has a value zero degrees, means for recording the intensity of the light sensed by the detector means at the datum position with the element in the light path, and means for controlling movement of the detector means to a position of equality whereat the intensity of light detected by the detector means without the element in the light path is the same as the intensity recorded with the detector at the datum position and with the element in the light path.

14. Apparatus as claimed in claim 13, including means for performing the calculation of the value of $$1/\cos^4\alpha$$

wherein: $\alpha$ is the value of $\Phi$ with the detector means at the position of equality.

15. Apparatus as claimed in claim 5, wherein the means for determining the position of the detector means along the track means is adapted to provide a signal indicative of angle $\Phi$ between the direction of the light when incident normally on the operative face of the detector means and the direction of the light incident on the operative face of the detector means at the position, including means for positioning the detector means at a datum position whereat the light is incident normally on the operative face of the detector means and the angle $\Phi$ has a value zero degrees, means for recording the intensity of the light sensed by the detector means at the datum position with the element in the light path, and means for controlling movement of the detector means to a position of equality whereat the intensity of light detected by the detector means without the element in the light path is the same as the intensity recorded with the detector at the datum position and with the element in the light path.

16. Apparatus as claimed in claim 15, including means for performing the calculation of the value of $$1/\cos^4\alpha$$

wherein: $\alpha$ is the value of $\Phi$ with the detector means at the position of equality.

17. Apparatus as claimed in any one of claims 1-5, 6,7, 11 through 14 and 16, including means for moving the detector means along the track means.

18. Apparatus for use in determining the optical transmission factor or density of a translucent element, including:
an integrating sphere having an inlet and an outlet defined by a knife edge;
means for introducing light of constant color and intensity into said integrating sphere through said inlet;
means for mounting the element to be tested in the path of light to the inlet of the sphere;
a detector having an operative face and adapted to provide a signal indicative of the intensity of light incident on it;
knife-edged mask means bounding an aperture on the operative face of the detector;
track means for mounting the detector for movement along a rectilinear path perpendicular to a radial line passing through the center of the sphere and the center of the outlet, with the operative face of the detector facing said outlet of the integrating sphere when the said radial line passes through said aperture on the operative face of the detector;

means for moving the detector along the track; and means for determining the position of the detector along said track.

19. Apparatus as claimed in claim 18, wherein said means for determining the position of the detector along the track means is adapted to provide a signal indicative of angle $\Phi$ between said radial line and a line intersecting the radial line, the outlet and the aperture.

20. Apparatus as claimed in claim 19, including:

means for positioning the detector at a datum position whereat the angle $\Phi$ has a value $\Theta$;

means for recording the intensity of light sensed by the detector at the datum position without the element in the light path; and means for controlling movement of the detector to a position of equality whereat the intensity of light detected by the detector with the element in the light path is the same as the intensity recorded with the detector at the datum position and without the element in the light path.

21. Apparatus as claimed in claim 20, including means for performing the calculation of the value of $$\frac{\cos^4\Theta}{\cos^4\alpha}$$

wherein:

$\Theta$ is the value of $\Phi$ when the detector is at the datum position; and $\alpha$ is the value of $\Phi$ when the detector is at the position of equality.

22. A method for determining the optical transmission factor of a translucent element using the cosine-to-the-fourth law, including the steps of:

providing an integrating sphere having an inlet and a knife-edged outlet;

providing a source of light of constant intensity and color;

directing light from said source into said sphere through the inlet;

providing detector means having an operative face and a knife-edged aperture on said face, the detector means being adapted to provide a signal indicative of the intensity of light incident on said operative surface;

providing means for moving the detector means along a rectilinear path perpendicular to a radial line passing through the center of the sphere and the outlet and so disposed that in one position of the detector means the operative face is intersected by and is perpendicular to said radial line;

positioning the detector means in a datum position on said path whereat the angle $\Phi$ between a line intersecting the outlet, the radial line and the operative face and the radial line has a value $\Theta$;

gaining from the detector means a signal indicative of the intensity of light incident on the operative face from the sphere when the detector is in the datum position;

inserting the element to be tested in the path of light from the light source to the sphere;

moving the detector means along the track until the signal generated by the detector means, when the element is in the light path, is the same as that generated by the detector means when at said datum position, the detector means then being in a position of equality in which the angle $\Phi$ has a value $\alpha$; and calculating with computer means the value of $$\frac{\cos^4\Theta}{\cos^4\alpha}$$

to determine the transmission factor of the element.

23. A method for determining the optical density of a translucent element, including performing the method as claimed in claim 22 for determining the transmission factor of the element and the further step of determining with computer means the value of the log of the reciprocal of the value of the transmission factor, to give the density.

24. A method as claimed in claim 22 or 23, wherein the value of $\Theta$ is close to but less than 90°.

25. A method for determining the optical transmission factor of a translucent element at a particular wavelength or band of wavelengths, including performing the method of claim 22 with the additional step of inserting a standard filter into the path of light from the source to the sphere prior to taking any measurements, said standard filter being adapted to pass substantially only the particular wavelength or band of wavelengths.

26. A method for determining the optical transmission factor of a translucent element using the cosine-to-the-fourth law, including the steps of:

providing a source of light of constant color and constant intensity;

providing an integrating sphere having an inlet and an outlet;

directing light from said source into said sphere through the inlet;

providing detector means having an operative face and a knife-edged aperture on said face, the detector means being adapted to provide a signal indicative of the intensity of light incident on the operative face;

providing means for moving the detector means along a rectilinear path perpendicular to a radial line passing through the center of the sphere and the outlet and so disposed that in one position of the detector means the operative face is intersected by and is perpendicular to said radial line;

positioning the detector means in a position on said path whereat the said radial line intersects and is perpendicular to the operative face;

inserting the element to be tested in the path of light from the sphere to the detector means;

recording the signal from the detector means;

withdrawing the element to be tested;

moving the detector means along said path to a position of equality at which the signal from the detector means is equivalent to the recorded signal;

determining the angle $\alpha$ between said radial line and the direction of light incident on the operative face when the detector means is in the position of equality; and calculating with computer means the value of $$1/\cos^4\alpha$$

to determine the transmission factor of the element.

27. A method for determining the optical transmission factor of a translucent element using the cosine-to-the-fourth law, including the steps of:

provmg a source of lambertain light of constant color and constant radiance;

providing detector means having an operative face and a knife-edged aperture on said face, the detector means being adapted to provide a signal indicative of the intensity of light incident on the operative face;

providing means for moving the detector means along a rectilinear path with the operative face of the detector means being in a plane parallel to the path, the path passing through a position in which the operative face of the detector means is perpendicular to light from the source;

positioning the detector means in said position on said path whereat light from the source is incident on the operative face of the detector means normally;

inserting the element to be tested in the path of light to the detector means;

recording the signal from the detector means;

withdrawing the element to be tested;

moving the detector means along said path to a position of equality at which the signal from the detector means is equivalent to the recorded signal;

determining the angle $\alpha$ between the direction of light incident normally on the operative face and the direction of light incident on the operative face when the detector means is in the position of equality; and calculating with computer means the value of $$1/\cos^4 \alpha$$

to determine the transmission factor of the element.

28. A method for determining the optical density of a translucent element, including performing the method of claim 26 or 27 for determining the transmission factor of the element and the further step of determining with computer means the value of the log of the reciprocal of the value of the transmission factor, to give the density.

* * * * *